United States Patent [19]

Wiest et al.

[11] Patent Number: 5,176,148
[45] Date of Patent: Jan. 5, 1993

[54] DEVICE FOR MEASURING THE URINE FLOW (UROFLOW) OF PATIENT

[75] Inventors: Peter P. Wiest; Hubert G. Fuchs, both of Berlin, Fed. Rep. of Germany

[73] Assignee: Friedhelm M. West, Putzbrun, Fed. Rep. of Germany

[21] Appl. No.: 590,211

[22] Filed: Sep. 28, 1990

[30] Foreign Application Priority Data

Sep. 30, 1989 [DE] Fed. Rep. of Germany ....... 3933025

[51] Int. Cl.⁵ ............................................. A61B 5/00
[52] U.S. Cl. ................................................... 128/760
[58] Field of Search .................. 128/760, 771; 73/861, 73/861.49, 861.54, 861.67

[56] References Cited

U.S. PATENT DOCUMENTS

| | | | |
|---|---|---|---|
| 3,871,230 | 3/1975 | Dye et al. | 128/771 |
| 3,871,231 | 3/1975 | Ciarico | 128/771 |
| 4,100,802 | 7/1978 | Layton | 128/771 |
| 4,238,448 | 12/1980 | Salvadori et al. | 128/760 |
| 4,554,687 | 11/1985 | Carter et al. | 128/760 |
| 4,589,280 | 5/1986 | Carter | 128/760 |
| 4,619,146 | 10/1986 | Teodorescu et al. | 73/861.54 |
| 4,732,160 | 3/1988 | Ask et al. | 128/760 |

*Primary Examiner*—Max Hindenburg

[57] ABSTRACT

The present invention pertains to a device for measuring the urine flow (Uroflow) of a patient, consisting of a measuring head provided with a funnel and an outflow port, and of an electronic evaluating unit.

In a prior-art measuring device of this class, the measuring head is mounted oscillatingly in a housing. This has disadvantages in terms of the mechanical design of the measuring device and the accuracy of measurement.

To simplify the mechanical design and to increase the accuracy of measurement, the measuring head 1 is provided, according to the present invention, with a slotted pitot tube 4 forming the outflow port 30 and with a pressure sensor 18 measuring the dynamic pressure, and the electronic evaluating unit 9 calculates the flow values from the flow-proportional dynamic pressure measured.

8 Claims, 1 Drawing Sheet

DEVICE FOR MEASURING THE URINE FLOW (UROFLOW) OF PATIENT

FIELD OF THE INVENTION

The present invention pertains to a device for measuring the urine flow (Uroflow) of a patient, consisting of a measuring head provided with a funnel and an outflow port and of an electronic evaluating unit.

BACKGROUND OF THE INVENTION

Prior-art measuring devices of this type measure as the physical parameter either the volume of the urine or the urine flow. This is performed according to a rotation-dynamic, gravimetric, or capacitive method, or, especially in the case of volume measurement, on the basis of the pressure of the liquid in a collecting beaker.

A measuring device of this class has been known from West German Patent Specification No. 30,07,855. Here, the measuring head is formed by a U-shaped measuring tube arranged essentially horizontally with a slight slope, through which the patient's urine flows and which is mounted inside a housing in a freely oscillating manner, with the funnel opening into the inlet port of the measuring head and the outflow port of the measuring head being arranged outside the housing. The patient's urine flows through the U-shaped measuring tube, which contains only a portion of the total amount of urine from a complete micturition, so that the measuring tube may be very small. However, the necessity to mount the U-shaped measuring tube in a freely oscillating manner inside the housing is disadvantageous.

A Uroflow measuring device of this class must also be able to be installed in the bathroom in the urological office, so that the urine can flow off directly. This permits only the use of a device which does not collect the urine. However, much greater importance is attached to accurate volume measurement in clinical urodynamic investigations. The urine is collected in a beaker at the measuring device. Furthermore, accurate representation of the flow curve as a function of time is very important for diagnosis. This is possible only when the flow is measured directly. When double differentiation is required for volume-based measurement to represent the increase in flow, the calculated result will be too inaccurate because of the effect of disturbances e.g., vibrations and wave movements of the liquid collected. Emptying of the collected liquid is too expensive in urological practice because of the great number of uroflow tests performed as a preliminary examination.

Volume calculation in flow-measuring devices is subject to great errors due to integration over time, precisely in the minimal flow range. Volume measurement is superior to flow measurement in this respect.

SUMMARY AND OBJECTS OF THE INVENTION

The basic task of the present invention is to provide a device for measuring the urine flow (Uroflow) of a patient, which combines the advantages of flow measurement with the advantages of volume measurement, wherein the device shall also be able to be used without urine collection in the urological practice, and the accuracy of the flow and volume measurements shall be sufficient for the clinical urodynamic investigations.

To accomplish this task according to the present invention, the measuring head is provided with a slotted pitot tube forming the outflow port and with a pressure sensor measuring the dynamic pressure, and the evaluating unit calculates the flow values from the measured flow-proportional dynamic pressure. This makes it possible to measure both the flow and the volume without moving parts, and the accuracy of flow and volume measurements is very high.

In a preferred embodiment, the measuring head has a vertical feed chamber connected to the funnel, an outflow chamber through which the slotted pitot tube passes, a vertical pressure-measuring chamber connected to the pressure sensor, and a horizontal distribution chamber connecting the feed chamber, the outflow chamber, and the pressure-measuring chamber, wherein the lower edges of the vertical slot in the pitot tube, of the feed chamber, and of the pressure chamber are arranged in a common horizontal plane, which forms the upper plane of the horizontal distribution chamber. A urine column is formed in the feed chamber, which is connected via the horizontal distribution chamber to both the outflow chamber traversed by the slotted pitot tube and the vertical pressure-measuring chamber. The liquid column in the feed chamber closes off the vertical pressure-measuring chamber, in which an air column, which transmits the dynamic pressure onto the pressure sensor, develops.

In another advantageous embodiment of the present invention, the vertical chamber is formed by a tray, which is flanged onto the measuring head detachably and in a liquid-tight manner, and into which the slotted pitot tube, which has a vertical slot of small width, is inserted.

To make it possible to measure both the flow and the volume as pressures proportional to the measured value with two identical pressure sensors, the measuring head with the outflow port is placed, according to the present invention, onto a collecting beaker, and the total volume of urine is measured with another pressure sensor arranged in the measuring head by measuring the filling height of the collecting reservoir on the basis of the static pressure of the urine collected in the collecting reservoir. The second pressure sensor measures the filling height of urine in the collecting reservoir via a measuring tube, which is flanged onto the measuring head and extends to the bottom of the collecting reservoir, and the second measuring transducer is placed at the top end of the collecting reservoir.

Finally, the measuring head and the two pressure sensors are accommodated in separate assembly units, which can easily be separated from each other. Thus, all the parts that come into contact with the urine, especially the measuring head itself with the collecting tray, the slotted pitot tube, and the measuring tube, as well as the collecting reservoir can be made of plastic, [which can be] cleaned and disinfected in a simple manner, and can be produced as interchangeable parts at low cost, whereas the pressure sensors are accommodated in a separate assembly unit.

BRIEF DESCRIPTION OF THE INVENTION

The present invention will be explained in greater detail below on the basis of the embodiment of a measuring device for measuring the urine flow (Uroflow) of a patient, which is represented in the drawing. The single Figure shows a vertical section through the measuring device.

DETAILED DESCRIPTION OF THE PREFERRED EMBODIMENTS

Figure 1:
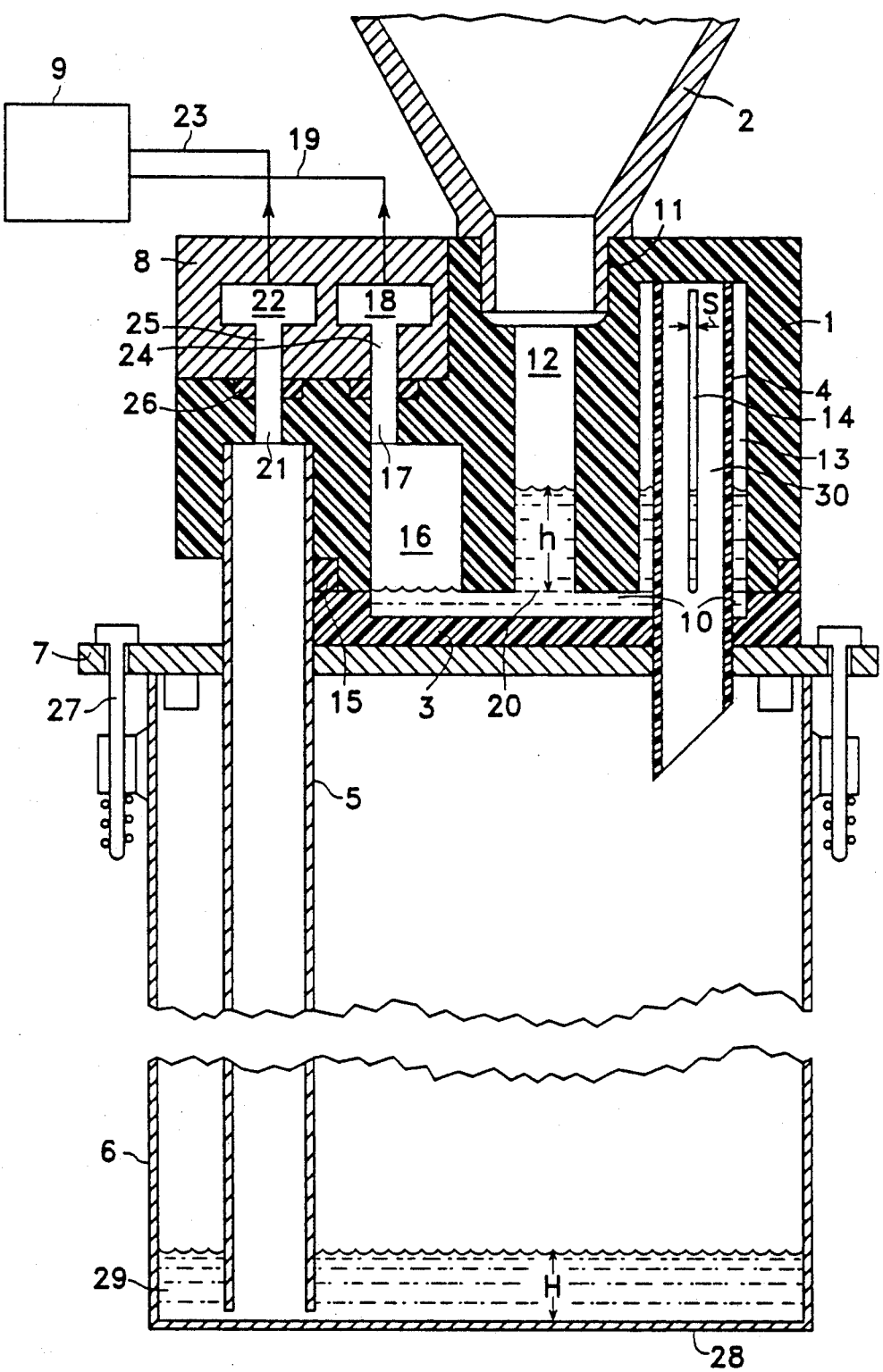

The measuring device comprises a measuring head 1, a funnel 2, a collecting tray 3 flanged onto said measuring head 1, a slotted tube 4, a measuring tube 5, a collecting reservoir 6 with a cover 7, a pressure sensor unit 8, as well as an electronic evaluating unit 9.

Said measuring head 1, which is preferably formed of plastic, carries on its top side said funnel 2, which is inserted into a receiving opening 11 of said measuring head 1. This receiving opening opens into a vertical feed chamber or intake chamber 12, which is open at its bottom end. An outflow chamber 13, into which said slotted pitot tube 4, which has a vertical slot 14 of width S, is inserted, extends in parallel to said feed chamber 12 in the vertical direction inside said measuring head 1. Said slotted pitot tube 4, which is also made of plastic, is permanently inserted in said collecting tray 3 made of plastic, which is connected to the lower side of said measuring head 1 in a liquid-sealing manner via a seal 15.

A vertical pressure-measuring chamber 16, which is open at the bottom and is connected at its top to said pressure sensor unit 8 via a communicating hole 17, is provided in parallel to said feed chamber 12 on the side of said measuring head 1 opposite said outflow chamber 13. Said pressure-measuring chamber 16 is associated in said pressure sensor unit 8 with a first pressure sensor 18, which is connected to said evaluating unit via an electrical connection line 19.

Said collecting tray 3 flanged under said measuring head 1 forms a horizontal distribution chamber 10, and the lower edges of said vertical slot 14 in said pitot tube 4, of said feed chamber 12, and of said pressure chamber 16 are located in a common horizontal plane 20, which forms the upper plane of said horizontal distribution chamber 10.

Said measuring head 1 also carries said measuring tube 5, which is parallel to said pitot tube 4 but is substantially longer, and is connected via a hole 21 to a second pressure sensor 22 located in said pressure sensor unit 8. Said second pressure sensor 22 is also connected electrically to said evaluating unit 9 via an electrical control line 23. Said pressure sensor unit 8 is a component that is separate from said measuring head 1, and its measuring holes 24 and 25 are connected to said measuring holes 17 and 21 of said pressure-measuring chamber 16 and of said measuring tube 5, respectively, in a pressure-tight manner. O-Rings 26 are used in the transition zone to achieve this.

Said measuring head 1 with its collecting tray 3, which closes the lower side, is placed onto said cover 7 of said collecting reservoir 6, and both said pitot tube 4 and said measuring tube 5 pass through said cover 7 in a sealing manner. Said cover 7 is firmly clamped onto said collecting reservoir 6 via spring-tensioned T-bolts 27. Said measuring tube 5 extends deep into said collecting reservoir 6, and the lower opening of said measuring tube 5 is arranged at a closely spaced location above the bottom 28 of said collecting reservoir 6.

The measuring device described operates as follows:

Said pressure sensor 22, which is connected to said measuring tube 5, measures the filling height H of urine 29 in said collecting reservoir 6 via the air column in said measuring tube 5.

Said pressure sensor 18 measures the column height h in said feed chamber 12 of said measuring head 1 via the air column in said pressure-measuring chamber 16. The instantaneous column height h is determined by the urine flow through said funnel 2 and said feed chamber 12 on the basis of the outflow behavior of urine through said slotted pitot tube 4 provided with said vertical slot 14. The inflow and outflow are at equilibrium at a given column head h. If friction and surface tension are ignored, the following relationships apply:

$$C_o = (2 \times g \times h')^{\frac{1}{2}} \text{ (Bernoulli equation)} \quad (1)$$

$$V^o = S \times {}_0[sigma]^h \times dh \quad (2)$$

$C_o$ = outflow velocity from said slot 14
g = gravitational acceleration (9.81 m/sec$^2$)
h' = column height over discharge jet
$V^o$ = flow through said slotted pitot tube (volume/sec) (mL/sec)
S = slot width
h = column height.

According to Equation (2), said electronic evaluating device 9 determines the flow from the measured column height h.

When said collecting reservoir 6 is used, said electronic evaluating unit 9 is able to check whether the flow curve has the correct height, based on the volume measurement, and to correct it accordingly. This is possible during the measurement after each major change in flow or after this measurement if the flow and volume values are stored in said electronic evaluating unit 9.

If the accuracy requirements are not too high, said collecting reservoir 6 may be omitted. Said measuring head 1 is now simply 15 installed in a bathroom. Said collecting reservoir 6 is used only to calibrate the flow measuring part in said measuring head 1 with said pressure sensor 18. To do so, a defined volume of water is poured through said funnel 2 at different flow velocities. After each change in flow, the mean previous flow is compared to the previous change in volume, and the correction value for this flow range is stored in a non-volatile memory of said electronic evaluating unit 9.

The possibility of separating said pressure sensor unit 8 containing said two pressure sensors 18 and 22 from said measuring head 1 is particularly advantageous. Together with said slotted pitot tube 4, said collecting tray 3 forming said distribution chamber 10 can also be separated from said measuring head 1 in a simple manner. This makes possible the simple cleaning and disinfection of the parts that come into contact with urine, while said pressure sensors 18 and 22 are not subjected to the risk of chemical or mechanical damage during these operations. The parts that come into contact with urine can also be made from plastic as inexpensive disposable parts, which are replaced after a short time of use, e.g., 1 week.

Said collecting reservoir 6 can be snapped in on said measuring head 1 without clearance by rotating it around its axis, and said measuring head 1 can in turn be mounted on a stand-mounted bracket.

If pressure sensors 18 and 22 of identical design are used, they can be supplied with energy by a pair of conductors. A computer circuit, which displays, via a printer, both the flow curve and the data, such as total volume, flow time, and rise time, is used as said electronic evaluating unit 8.

We claim:

1. A device for measuring urine flow of a patient, comprising: a measuring head with a funnel, the measuring head defining a vertical intake chamber communicating with said funnel, an outflow chamber provided with a drain pipe connection, said drain pipe connection including a slotted tube with vertical slot providing communication between said outflow chamber and said drain pipe connection, a pressure measuring chamber and a distribution chamber connecting each of said intake chamber, said outflow chamber and said pressure measuring chamber; pressure sensing means connected to said pressure-measuring chamber for measuring a dynamic pressure; and, evaluating means connected to said pressure sensing means for determining a flow value based on the dynamic pressure, that is proportional to the flow, sensed by said pressure sensing means.

2. A device according to claim 1, wherein said slotted tube is formed as a pitot tube, said vertical slot having lower edges lying in a common horizontal plane with an upper plane of the horizontal distribution chamber and the connection of said horizontal distribution chamber with said pressure-measuring chamber and said intake chamber.

3. A device according to either claim 1 or claim 2, wherein said distribution chamber is formed by a tray element which is flanged to a lower surface of said measuring head in a detachable, liquid-tight manner, said slotted tube being inserted through an opening of said tray element.

4. A device according to either claim 1 or claim 2, wherein said vertical slot of said slotted tube has a predetermined width (S).

5. A device according to either claim 1 or claim 2, wherein said slotted tube forms an outflow port connected to a collecting beaker, said measuring head being connected to an additional pressure sensor, a collecting reservoir extending from said collecting beaker to said measuring head for sensing pressure in said collecting reservoir, at said additional pressure sensor to measure a filling height of said collecting reservoir via a static pressure of urine collected in the collecting reservoir.

6. A device according to claim 5, wherein said pressure sensor and said additional pressure sensor are arranged in a common pressure sensing housing, said common pressure sensing housing being detachably connected to said measuring head.

7. A device according to claim 5, wherein said additional pressure sensor is provided with a measuring tube extending to a location adjacent a bottom of said collecting beaker.

8. A device according to claim 5, wherein said evaluating means determines a total volume of urine by measuring a filling height (H) via a static pressure of liquid collected in said collecting reservoir based on pressure sensed by said additional pressure sensor, said evaluating means determining a flow proportional to a dynamic pressure measured at said slotted tube based on a pressure measured by said pressure sensor, said evaluating means calculating a flow value and simultaneously correcting said calculated flow value based on volume values determined from pressure sensed by said pressure sensor.

* * * * *

UNITED STATES PATENT AND TRADEMARK OFFICE
CERTIFICATE OF CORRECTION

PATENT NO.   :   5,176,148
DATED        :   January 5, 1993
INVENTOR(S)  :   Wiest et al It is certified that error appears in the above-identified patent and that said Letters Patent is hereby corrected as shown below:

On the title page, Assignee should read:

[73] Assignee:   Friedhelm M. Wiest, Putzbrunn,
                 Fed. Rep. of Germany On the title page, please insert the following:

Attorney, Agent or Firm - McGlew and Tuttle, P.C.

Signed and Sealed this

Second Day of November, 1993

Attest:

BRUCE LEHMAN

Attesting Officer    Commissioner of Patents and Trademarks